US00PP12629P2

(12) United States Plant Patent
Geerlings

(10) Patent No.: US PP12,629 P2
(45) Date of Patent: May 21, 2002

(54) SIDALCEA PLANT NAMED 'LITTLE PRINCESS'

(75) Inventor: Aad Geerlings, Lisserbroek (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,561

(22) Filed: Dec. 29, 1999

(51) Int. Cl.[7] ..... A01H 5/00
(52) U.S. Cl. ..... Plt./263
(58) Field of Search ..... Plt./263

(56) References Cited

PUBLICATIONS

GTITM UPOVROM Citation for 'Little Princess' as per NL PBR SDC0001; Nov. 6, 1997.*

GTITM UPOVROM Citation for 'Little Princess' as per QZ PBR 980544; Apr. 8, 1998.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Sidalcea plant named 'Little Princess', characterized by its upright plant habit; compact growth habit; very freely and uniformly flowering; and attractive large light pink-colored flowers.

2 Drawing Sheets

BACKGROUND OF THE INVENTION

The present invention relates to a new and distinct cultivar of Sidalcea plant, botanically known as *Sidalcea oregana*, and hereinafter referred to by the cultivar name 'Little Princess'.

The new cultivar is a product of a planned breeding program conducted by the Inventor in Hummelo, The Netherlands. The objective of the breeding program was to develop compact Sidalcea cultivars.

The new cultivar originated from a cross made by the Inventor in 1994 of two unidentified seedling selections of *Sidalcea oregana*.

The cultivar 'Little Princess' was discovered and selected by the Inventor as a flowering plant within the progeny of the stated cross in a controlled environment in Hummelo, The Netherlands.

Asexual propagation of the new cultivar by cuttings and root divisions harvested at Hummelo, The Netherlands, has shown that the unique features of this new Sidalcea are stable and reproduced true to type in successive generations.

SUMMARY OF THE INVENTION

Plants of the cultivar 'Little Princess' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Little Princess'. These characteristics in combination distinguish 'Little Princess' as a new and distinct cultivar:

1. Upright plant habit.

2. Compact growth habit.
3. Very freely and uniformly flowering.
4. Attractive large light pink-colored flowers.

Compared to plants of the parent seedling selections, plants of the new Sidalcea are more compact, shorter and have lighter pink flowers.

Plants of the new Sidalcea can also be compared to the *Sidalcea oregana* cultivar 'My Love', not patented. However, in side-by-side comparisons conducted by the Inventor in Hummelo, The Netherlands, plants of the new Sidalcea are more compact, shorter and differ from plants of the cultivar 'My Love' in flower shape.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Sidalcea.

The photograph on the first sheet comprises a side perspective view of typical plants of the new Sidalcea.

The photograph at the top of the second sheet comprises a close-up view of a typical flowers of the new Sidalcea at various stages of development.

The photograph at the bottom of the second sheet comprises a close-up view of a typical leaf of the new Sidalcea.

DETAILED BOTANICAL DESCRIPTION

In the following description, color references are made to The Royal Horticultural Society Colour Chart except where general terms of ordinary dictionary significance are used. Plants used for the description were about one year-old and grown in 17-cm containers under outdoor production conditions which closely approximate commercial production conditions during the spring and summer in Hummelo, The Netherlands.

Botanical classification: *Sidalcea oregana* cultivar 'Little Princess'.

Parentage:

*Female parent.*—Unidentified seedling selection of *Sidalcea oregana.*

*Male parent.*—Unidentified seedling selection of *Sidalcea oregana.*

Propagation:

*Type.*—By cuttings.

*Time to rooting.*—About 4 months at temperatures about 15° C.

*Root description.*—Fleshy and fibrous.

Plant description:

*Crop time.*—From cuttings, about 40 weeks are required to produce fully-grown flowering plants in 17-cm containers.

*Form.*—Upright, compact; conical.

*Branching habit.*—Moderate branching; typically about five lateral branches.

*Plant height.*—About 60 cm.

*Area of spread.*—About 30 cm.

*Vigor.*—Moderate to vigorous.

*Lateral branches.*—Length: About 30 to 45 cm. Diameter: About 4 mm. Internode length: About 10 cm. Texture: Very sparsely covered with very short (less than 0.5 mm) white hairs. Color: 138B.

*Foliage description.*—Arrangement: Alternate; single. Length: About 10 cm. Width: About 1.3 cm. Shape: Divided to the base; three, five or seven-lobed. Apex: Acute. Base: Attenuate. Margin: Entire. Texture: Smooth to slightly rugose; main veins and margin very sparsely covered with very short (less than 0.5 mm) white hairs. Color: Young and mature foliage, upper surface: 137A. Young and mature foliage, lower surface: 137C to 138A. Venation, upper surface: 137A. Venation, lower surface: 137C to 138A. Petiole: Length: About 5 cm. Diameter: About 2 mm. Color: 137C to 138A.

Flower description:

*Flower type and habit.*—Numerous single cupped flowers arranged in spicate racemes. Very freely flowering with about 600 flowers and flower buds per plant.

*Natural flowering season.*—Continuously flowering typically during the summer.

*Flower longevity.*—Flowers last about one week on the plant and about three or four days as a cut flower. Flowers self-cleaning.

*Fragrance.*—Faint dusty and slightly unpleasant.

*Flower buds (about four days before opening).*—Length: About 1.3 cm. Diameter: About 6 mm. Shape: Ovate. Rate of opening: About three to four weeks from visible bud to fully opened flower. Color: Corolla, 62A; calyx, 139C.

*Flower size.*—Length (height): About 1 cm. Diameter: About 3.8 cm.

*Petals.*—Shape: Roughly cordate. Apex: Rounded to praemorse or retuse. Base: Attenuate. Margin: Entire. Length: About 1.7 cm. Width: About 1.5 cm. Texture: Smooth. Color: When opening, upper surface: 62A. When opening, lower surface: 62B. Fully opened flower, upper surface: 62B fading to white towards margin. Fully opened flower, lower surface: 62C to 62D.

*Calyx.*—Length: About 5 mm. Width: About 1.4 cm. Number of sepals: Five. Sepal shape: Lanceolate. Sepal apex: Acuminate. Sepal margin: Entire. Sepal texture: Dull with very short (less than 0.5 mm) white hairs. Sepal color: Both surfaces, 139C.

*Pedicels.*—Length: About 2.5 mm. Angle: About 45° to vertical. Strength: Moderate to strong. Color: 137C.

*Reproductive organs.*—Stamens: Anther attachment: Dorsifixed. Anther length: Less than 0.2 mm. Anther color: Brownish pink. Pollen amount: Moderate. Pollen color: Creamy white. Pistils: Pistil number: Eight. Pistil length: About 6 mm. Stigma shape: Elongated. Stigma color: 62C. Style length: About 2 mm. Style color: 62C. Ovary color: 141D.

*Seed.*—Seed production has not been observed to date.

Disease resistance: Under commercial conditions, plants of the new Sidalcea have been shown to be slightly susceptible to pathogens common to Sidalcea.

It is claimed:

1. A new and distinct cultivar of Sidalcea plant named 'Little Princess', as illustrated and described.

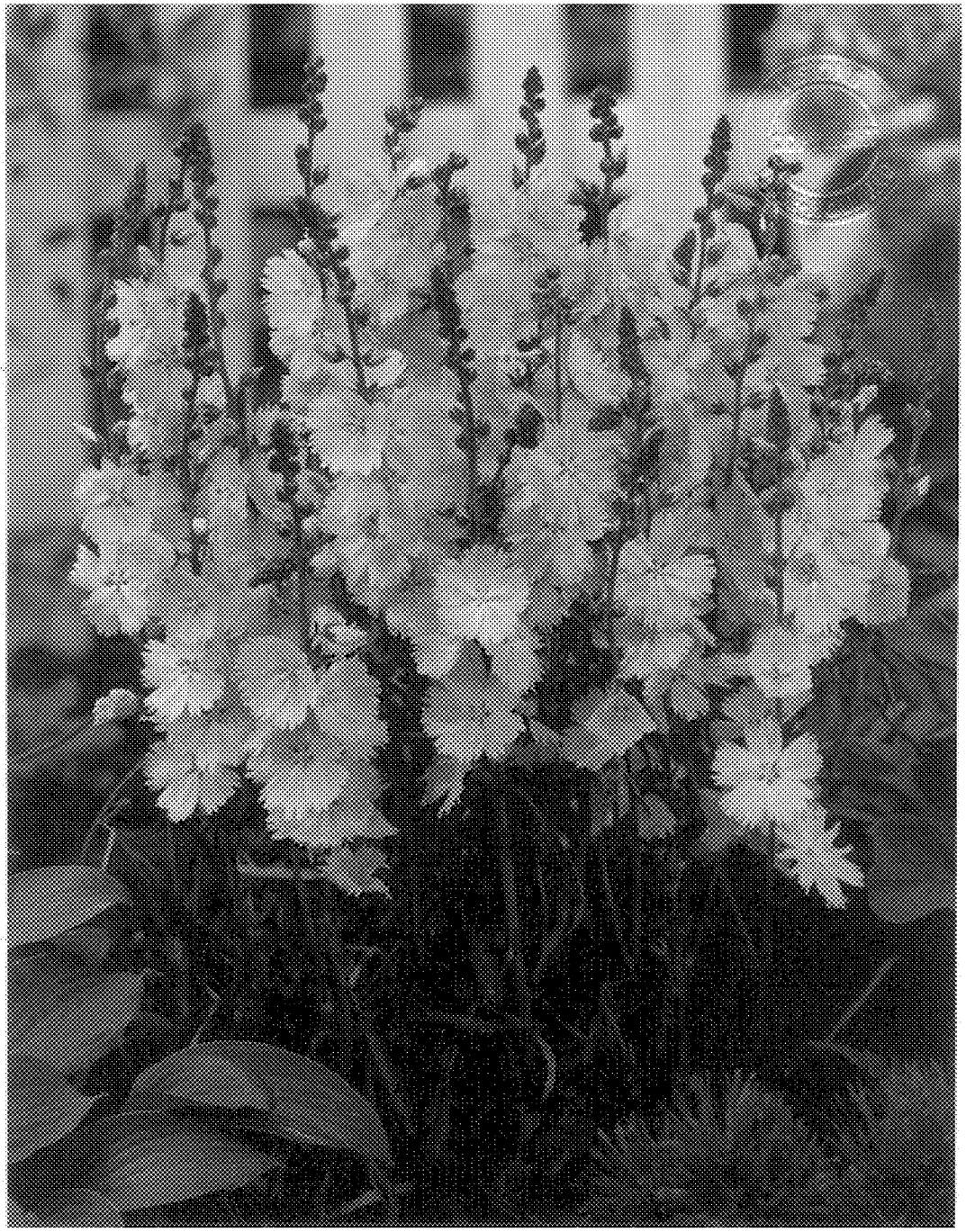

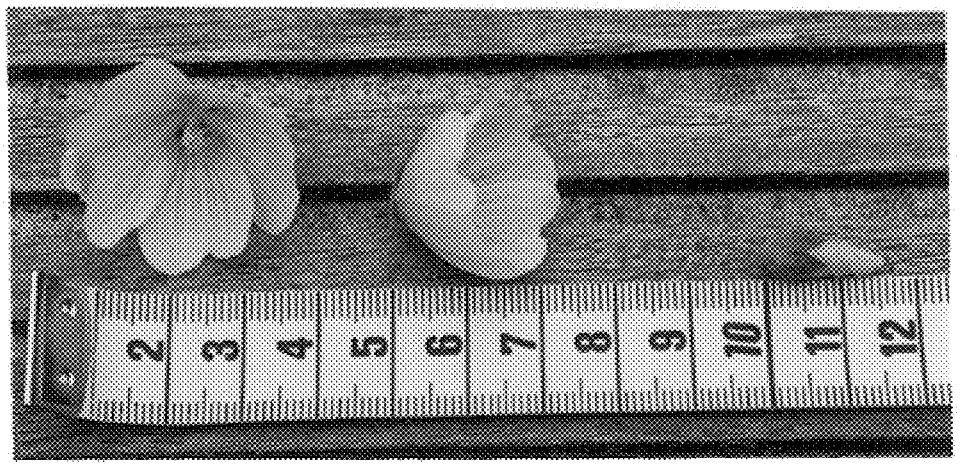
2
3
4
5
6
7
8
9
10
11
12
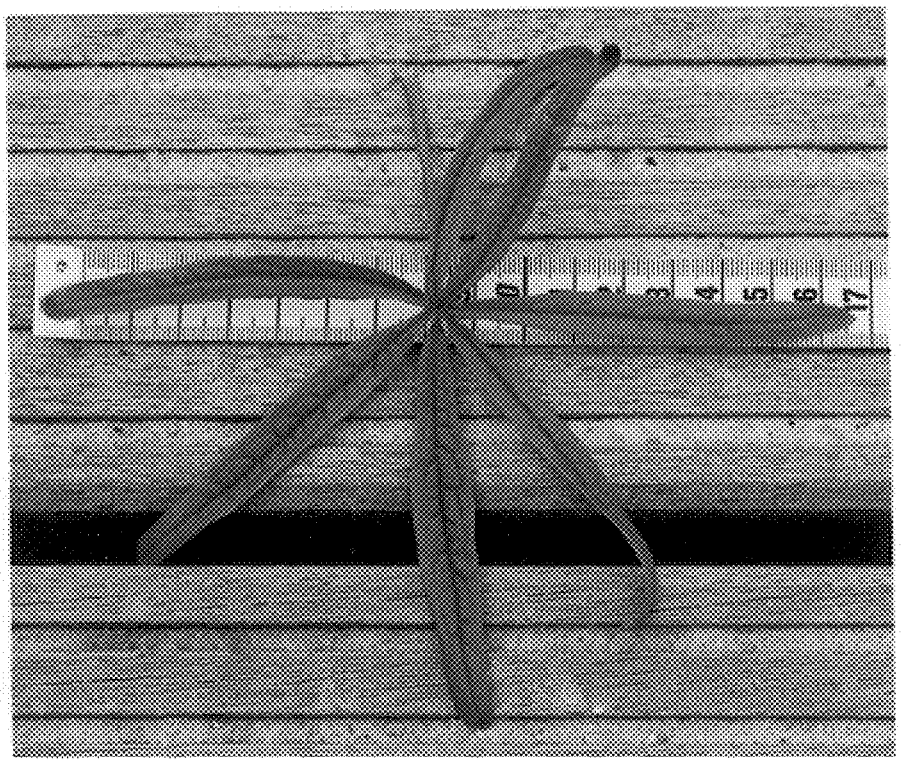

* * * * *